(12) United States Patent
Miracle et al.

(10) Patent No.: US 6,551,987 B1
(45) Date of Patent: Apr. 22, 2003

(54) PRO-FRAGRANCES

(75) Inventors: Gregory Scott Miracle, Hamilton, OH (US); Lon Montgomery Gray, Florence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/030,758

(22) PCT Filed: Apr. 14, 2000

(86) PCT No.: PCT/US00/10166

§ 371 (c)(1),
(2), (4) Date: Oct. 22, 2001

(87) PCT Pub. No.: WO00/63339

PCT Pub. Date: Oct. 26, 2000

Related U.S. Application Data

(60) Provisional application No. 60/130,108, filed on Apr. 20, 1999.

(51) Int. Cl.[7] ............ A61K 7/46; C07C 43/32; C07C 211/00
(52) U.S. Cl. ............ 512/2; 512/8; 512/12; 512/22; 512/24; 564/454; 568/591
(58) Field of Search ............ 568/591; 512/2, 512/8, 12, 22, 24; 564/454

(56) References Cited

U.S. PATENT DOCUMENTS 5,378,468 A * 1/1995 Suffis et al.

OTHER PUBLICATIONS

Schulte—Elte et al, Synthetic Transition of Ionone to Damascones, 1973, Helvetic Chimica Acta, pp. 310–320. with abstract.*

* cited by examiner

Primary Examiner—Johann Richter
Assistant Examiner—Paul A. Zucker
(74) Attorney, Agent, or Firm—James F. McBride; Kim W. Zerby; Steven W. Miller

(57) ABSTRACT

The present invention relates to fragrance delivery systems which comprise: a) one or more pro-fragrances having formula (I) wherein $G^1$ and $G^2$ are methyl, or a cyclic hydrocarbyl unit derived from the isomers of ionone and/or damascone; R and $R^1$ are each independently $C_1$–$C_{22}$ substituted or unsubstituted, branched or unbranched alkyl, $C_2$–$C_{22}$ substituted or unsubstituted, branched or unbranched alkenyl, $C_2$–$C_{20}$ substituted or unsubstituted, branched or unbranched hydroxyalkyl, $C_7$–$C_{20}$ substituted or unsubstituted alkylenearyl, $C_3$–$C_{20}$ substituted or unsubstituted cycloalkyl, alkyleneoxy, $C_6$–$C_{20}$ aryl, $C_5$–$C_{20}$ heteroaryl comprising one or more heteroatoms selected from the group consisting of nitrogen, oxygen, sulfur, and mixtures thereof; two of the units $Y^1$, $Y^2$, R or $R^1$ can be taken together to form one or more aromatic or non-aromatic, heterocyclic or non-heterocyclic, single rings, fused rings, bicyclo rings, spiroannulated rings, or mixtures thereof, said rings comprising from 3 to 20 carbon atoms and one or more heteroatoms selected from the group consisting of nitrogen, oxygen, sulfur, and mixtures thereof; b) one or more aldehyde releasing oxazolidine pro-fragrances; and c) the balance carriers, pro-fragrances, pro-accords, other perfume ingredients.

11 Claims, No Drawings

PRO-FRAGRANCES

CROSS REFERENCE TO RELATED APPLICATIONS

This application is an entry into the U.S. National Stage under 35 U.S.C. §371 of PCT International Application Serial No. PCT/US00/10166, filed Apr. 14, 2000, which claims priority under PCT Article 8 and 35 U.S.C. §119(e) to U.S. Provisional Application Serial No. 60/130,108, filed Apr. 20, 1999, (now abandoned).

FIELD OF THE INVENTION

The present invention relates to β-amino ketone pro-fragrances which are capable of delivering fragrance raw material ketones, preferably α,β-unsaturated ketones, inter alia, damascones, ionones, to a situs, especially to human-.skin wherein said pro-fragrances release the fragrance raw material ketones providing the user with extended aesthetic benefits.

BACKGROUND OF THE INVENTION

Humans have applied scents and fragrances to their skin since antiquity. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modern chemistry, individual components responsible for the odor properties of these resins, gums and oils were isolated and subsequently characterized. Aside from common "perfume vehicles" inter alia, fine perfumes, colognes, eau de toilettes, and after-shave lotions, a wide variety of personal care or personal hygiene items also deliver for aesthetic reasons fragrance notes, accords, or fragrance "characteristics".

It is well known that mixtures of perfume or fragrance raw materials when deposited on the skin lose intensity and may change character with time, mainly due to factors such as differential evaporation and skin penetration. Many attempts have been made to minimize these drawbacks, but so far without notable success. Particularly, efforts have been made to prolong the diffusion, as well as to improve other characteristics of fragrance materials, by e.g. increasing the fragrance raw material concentration or by using additives such as silicones, glycerol, polyethylene glycols and so on. Such additions, however, have never been adequate to increase the longevity of the fragrance odor.

Recently the advent of pro-fragrance and pro-accords have afforded the fine fragrance and perfume formulator with the ability to deliver fragrance raw materials to human skin in a controllable manner thus enhancing the longevity of the fragrance. Most pro-accords inter alia orthoesters, are suitable for delivery fragrance raw material alcohols and esters. Aldehydes and ketones have been delivered via acetals and ketals respectively, however, both of these pro-fragrance materials depend upon the modification of the carbonyl moiety and the rate of ketone fragrance raw material release has been difficult to fine tune to the subtleties of fine fragrance and perfume accords.

Accordingly, there remains a need in the art for a ketone fragrance raw material releasing pro-fragrance which can be formulated into fine fragrances, perfumes, personal care and personal hygiene products wherein the ketone fragrance raw material components can be released in a highly controllable manner to provide enhanced fragrance longevity.

SUMMARY OF THE INVENTION

The present invention meets the aforementioned needs in that it has been surprisingly discovered that certain ketone fragrance raw materials inter alia derivatives of ionone and damascone can be controllably released from novel β-amino ketone pro-fragrances. The β-amino pro-fragrances, preferably β-amino ketone pro-fragrances, of the present invention are useful in fragrance delivery systems which deliver fine fragrances with an enhanced perfume longevity.

A first aspect of the present invention relates to compositions comprising:

A) from 0.01% by weight, of a pro-fragrance component comprising:
  a) at least 0.01% by weight, of an β-amino ketone pro-fragrance component, said pro-fragrance having the formula:

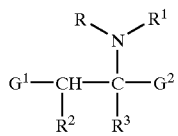

wherein $G^1$ is —CN, —C(O)Y$^1$, —CO$_2$Y$^1$, and mixtures thereof; $G^2$ is $G^1$, $Y^2$, or mixtures thereof, $Y^1$ and $Y^2$ are each independently $C_1$–$C_{18}$ alkyl, $C_1$–$C_{18}$ alkenyl, $C_1$–$C_{15}$ cycloalkyl, $C_1$–$C_{15}$ cycloalkenyl, $C_6$–$C_{15}$ aryl, $C_6$–$C_{15}$ alkyl substituted aryl, and mixtures thereof; R and $R^1$ are each independently $C_1$–$C_{22}$ substituted or unsubstituted, branched or unbranched alkyl, $C_2$–$C_{22}$ substituted or unsubstituted, branched or unbranched alkenyl, $C_2$–$C_{20}$ substituted or unsubstituted, branched or unbranched hydroxyalkyl, $C_7$–$C_{20}$ substituted or unsubstituted alkylenearyl, $C_3$–$C_{20}$ substituted or unsubstituted cycloalkyl, alkyleneoxy units having the formula:

wherein $R^4$ is $C_2$–$C_4$ alkylene, $R^5$ is hydrogen, $C_1$–$C_4$ alkyl, and mixtures thereof, x is from 1 to 6; $C_6$–$C_{20}$ aryl, $C_5$–$C_{20}$ heteroaryl comprising one or more heteroatoms selected from the group consisting of nitrogen, oxygen, sulfur, and mixtures thereof; two of the units $Y^1$, $Y^2$, R or $R^1$ when taken together form one or more aromatic or non-aromatic, heterocyclic or non-heterocyclic, single rings, fused rings, bicyclo rings, spiroannulated rings, or mixtures thereof, said rings comprising from 3 to 20 carbon atoms and one or more heteroatoms selected from the group consisting of nitrogen, oxygen, sulfur, and mixtures thereof; and $R^2$ and $R^3$ are hydrogen;

b) at least 0.01% by weight, of an aldehyde or ketone releasing pro-fragrance component, said pro-fragrance having the formula:

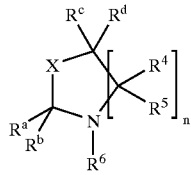

wherein said pro-fragrance or pro-accord releases an aldehyde or a ketone fragrance raw material, wherein X is oxygen or sulfur; $R^a$ is:

i) $C_6$–$C_{22}$ substituted or unsubstituted linear alkyl;
ii) $C_6$–$C_{22}$ substituted or unsubstituted branched alkyl;
iii) $C_6$–$C_{22}$ substituted or unsubstituted linear alkenyl;
iv) $C_6$–$C_{22}$ substituted or unsubstituted branched alkenyl;
v) $C_6$–$C_{22}$ substituted or unsubstituted cycloalkyl;
vi) $C_6$–$C_{22}$ substituted or unsubstituted branched cycloalkyl;
vii) $C_6$–$C_{22}$ substituted or unsubstituted cycloalkenyl;
viii) $C_6$–$C_{22}$ substituted or unsubstituted branched cycloalkenyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
xii) and mixtures thereof;
$R^b$ is:
i) hydrogen;
ii) $C_1$–$C_{10}$ substituted or unsubstituted linear alkyl;
iii) $C_3$–$C_{10}$ substituted or unsubstituted branched alkyl;
iv) $C_2$–$C_{10}$ substituted or unsubstituted linear alkenyl;
v) $C_3$–$C_{10}$ substituted or unsubstituted branched alkenyl;
vi) $C_3$–$C_{15}$ substituted or unsubstituted cycloalkyl;
vii) $C_4$–$C_{15}$ substituted or unsubstituted branched cycloalkyl;
viii) $C_4$–$C_{15}$ substituted or unsubstituted cycloalkenyl;
ix) $C_5$–$C_{15}$ substituted or unsubstituted branched cycloalkenyl;
x) $C_6$–$C_{15}$ substituted or unsubstituted aryl;
xi) $C_6$–$C_{22}$ substituted or unsubstituted heterocyclicalkyl;
xii) $C_6$–$C_{22}$ substituted or unsubstituted heterocyclicalkenyl;
$R^a$ and $R^b$ when taken together form a substituted or unsubstituted ring having in the ring from 3 to 10 carbon atoms; and
each $R^c$, $R^d$, $R^6$ and each $R^4$ and $R^5$ pair are independently:
i) $R^b$;
ii) hydroxyl;
iii) a carbonyl comprising unit having the formula:

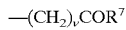

wherein $R^7$ is:
a) —OH;
b) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof;
c) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
d) $C_1$–$C_{22}$ substituted or unsubstituted linear alkyl;
e) $C_1$–$C_{22}$ substituted or unsubstituted branched alkyl;
f) $C_2$–$C_{22}$ substituted or unsubstituted linear alkenyl;
g) $C_3$–$C_{22}$ substituted or unsubstituted branched alkenyl;
h) $C_3$–$C_{22}$ substituted or unsubstituted cycloalkyl;
i) $C_6$–$C_{22}$ substituted or unsubstituted aryl;
j) $C_6$–$C_{22}$ substituted or unsubstituted heterocyclicalkyl;
k) $C_6$–$C_{22}$ substituted or unsubstituted heterocyclicalkenyl;
the index v is from 0 to 22;
iv) alkyleneoxy units having the formula:

$$-(CR^{10}R^{11})_y(CHR^{12}CHR^{13}O)_zR^{14}$$

wherein each $R^{10}$, $R^{11}$, and $R^{12}$ is independently;
a) hydrogen;
b) —OH;
c) $C_1$–$C_4$ alkyl;
d) or mixtures thereof;
$R^{13}$ is:
a) hydrogen;
b) $C_1$–$C_4$ alkyl;
c) or mixtures thereof;
$R^{14}$ is:
a) hydrogen;
b) $C_1$–$C_4$ alkyl;
c) or mixtures thereof;
$R^{10}$ and $R^{11}$ when taken together form a $C_3$–$C_6$ spiroannulated ring, carbonyl unit, or mixtures thereof; y has the value from 0 to 10, z has the value from 1 to 50;
v) any two $R^c$, $R^d$, $R^4$, $R^5$, or $R^6$ units when taken together form:
a) a carbonyl moiety;
b) a $C_3$–$C_6$ spiroannulated ring;
c) a heterocyclic aromatic ring comprising from 5 to 7 atoms;
d) a non-heterocyclic aromatic ring comprising from 5 to 7 atoms;
e) a heterocyclic ring comprising from 5 to 7 atoms;
f) a non-heterocyclic ring comprising from 5 to 7 atoms;
g) or mixtures thereof;
vi) and mixtures thereof; and
the index n is an integer from 1 to 3; and
B) optionally from 1% by weight, a fragrance raw material component comprising:
i) optionally at least 1% by weight, of a mixture of one or more base note fragrances;
ii) optionally at least 1% by weight, of a mixture of one or more top or middle note fragrances;
iii) optionally the balance carriers, fixatives, and other adjunct ingredients.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to fragrance delivery systems which comprise one or more β-amino ketone pro-fragrances of damascones, ionones and their isomers. The pro-fragrances of the present invention are suitable for use in fragrance delivery systems which are capable in delivering enhanced fragrance benefits to fine fragrances and perfumes as well as personal care and personal hygiene articles.

The β-amino pro-fragrances of the present invention have the formula:

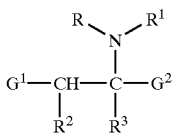

wherein $G^1$ is —CN, —C(O)Y$^1$, —CO$_2$Y$^1$, and mixtures thereof; $G^2$ is $G^1$, $Y^2$, or mixtures thereof; $Y^1$ and $Y^2$ are each independently $C_1$–$C_{18}$ alkyl, $C_1$–$C_{18}$ alkenyl, $C_1$–$C_{15}$ cycloalkyl, $C_1$–$C_{15}$ cycloalkenyl, $C_6$–$C_{15}$ aryl, $C_6$–$C_{15}$ alkyl substituted aryl, and mixtures thereof; and $R^2$ and $R^3$ are hydrogen.

R and $R^1$ are each independently $C_1$–$C_{22}$ substituted or unsubstituted, branched or unbranched alkyl, $C_2$–$C_{22}$ substituted or unsubstituted, branched or unbranched alkenyl, $C_2$–$C_{20}$ substituted or unsubstituted, branched or unbranched hydroxyalkyl, $C_7$–$C_{20}$ substituted or unsubstituted alkylenearyl, $C_3$–$C_{20}$ substituted or unsubstituted cycloalkyl, alkyleneoxy units having the formula:

—(R$^4$O)$_x$R$^5$ wherein $R^4$ is $C_2$–$C_4$ alkylene, $R^5$ is hydrogen, $C_1$–$C_4$ alkyl, and mixtures thereof, x is from 1 to 6; $C_6$–$C_{20}$ aryl, $C_5$–$C_{20}$ heteroaryl comprising one or more heteroatoms selected from the group consisting of nitrogen, oxygen, sulfur, and mixtures thereof; two of the units $Y^1$, $Y^2$, $R^1$ or can be taken together to form one or more aromatic or non-aromatic, heterocyclic or non-heterocyclic, single rings, fused rings, bicyclo rings, spiroannulated rings, or mixtures thereof, said rings comprising from 3 to 20 carbon atoms and one or more heteroatoms selected from the group consisting of nitrogen, oxygen, sulfur, and mixtures thereof.

In another aspect of Applicants' invention the β-amino pro-fragrances of the present invention have the formula:

wherein $Y^1$ and $Y^2$ are each methyl or a cycloalkenyl unit selected from the group consisting of:

i) 2,6,6-trimethylcyclohex-2-enyl having the formula:

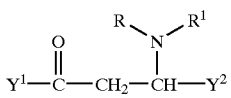

ii) 2,6,6-trimethylcyclohex-1-enyl having the formula:

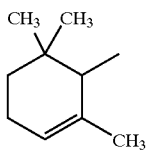

iii) 2-methylene-6,6-dimethylcyclohexanyl having the formula:

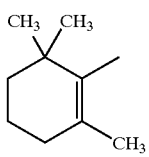

iv) 2,6,6-trimethylcyclohex-3-enyl having the formula:

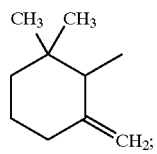

v) and mixtures thereof;

provided at least one $Y^1$ or $Y^2$ is methyl and both $Y^1$ and $Y^2$ are not each methyl, R and $R^1$ are not both hydrogen.

The following are the common chemical names for the damascones and ionones which are delivered by the pro-fragrances of the present invention; 1-(2,6,6-trimethylcyclohex-2-enyl)-2-butene-1-one(α-damascone), 1-(2,6,6-trimethylcyclohex-1-enyl)-2-butene-1-one(β-damascone), 1-(2-methylene-6,6-dimethylcyclohexanyl)-2-butene-1-one(γ-damascone), 1-(2,6,6-trimethylcyclohex-3-enyl)-2-butene-1-one (δ-damascone), 4-(2,6,6-trimethylcyclohex-2-enyl)-3-butene-2-one(α-ionone), 4-(2,6,6-trimethylcyclohex-1-enyl)-3-butene-2-one(β-ionone), 4-(2-methylene-6,6-dimethylcyclohexanyl)-3-butene-2-one (γ-ionone).

Further preferred ketones which can be delivered by the β-amino ketone pro-fragrances of the present invention include 4-(2,6,6-trimethyl-2-cyclohexen-1-yl)-3-methyl-3-buten-2-one, 1-(2,6,6-trimethyl-2-cyclohexen-1-yl)-1,6-heptandien-3-one, 4-(2,5,6,6-tetramethyl-2-cyclohexen-1-yl)-3-methyl-3-buten-2-one, 2-pentyl-2-cyclopenten-1-one, 2-hexyl-2-cyclopenten-1-one, cis-3-methyl-2-(2-pentenyl)-2-cyclopenten-1-one, 6-(2-propenyl)-5-methyl-2-(1-methylethylidene)cyclohexanone, 4-(4-methoxy)phenyl-3-buten-2-one, 2,5,5-trimethyl-2,6-heptadien-4-one, and 2-methyl-6-(4-methylcyclohex-3-enyl)-2,5-heptadien-4-one.

An example of a β-amino ketone pro-fragrance according to the present invention includes 1-(2,6,6-trimethyl-3-cyclohexen-1-yl)-3-N-(2-hydroxyethyl)-N-phenylmethyl-1-butanone having the formula:

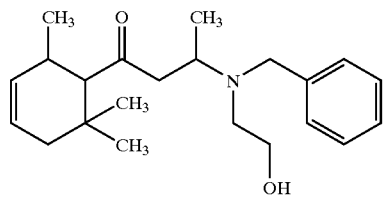

1-(2,6,6-trimethyl-3-cyclohexen-1-yl)-3-N,N-di(2-hydroxyethyl)-1-butanone having the formula:

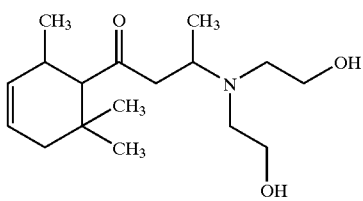

1-(2,6,6-trimethyl-3-cyclohexen-1-yl)-3-N,N-bis(5-hydroxy-3-oxapentyl)-1-butanone having the formula:

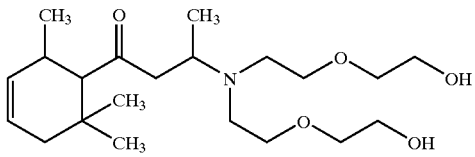

and 2-hexyl-3-di(2-hydroxyethyl)aminocyclopentanone having the formula:

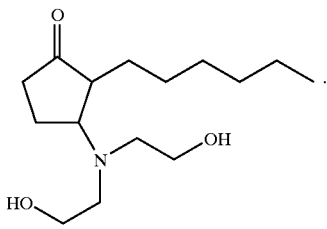

Aldehyde and Ketone Releasing Pro-fragrances

The fragrance delivery systems of the present invention comprise one or more heterocyclic aldehyde-releasing and/or ketone-releasing pro-fragrances preferably oxazolidines, tertahydro-1,3-oxazines, thiazolidines, or tetrahydro-1,3-thiazines, more preferably oxazolidines, or tertahydro-1,3-oxazines, most preferably oxazolidines.

The pro-fragrances or pro-accords which are suitable for use in the fragrance delivery systems described herein have the formula:

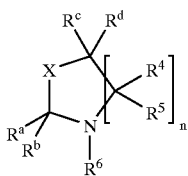

and are capable of releasing an aldehyde fragrance raw material having the formula:

or a ketone fragrance raw material having the formula:

For the purposes of the fragrance delivery systems which comprise one or more heterocyclic pro-fragrances or pro-accords, $R^a$ units are defined herein as:

i) $C_6$–$C_{22}$, preferably $C_6$–$C_{18}$, more preferably $C_6$–$C_{15}$ substituted or unsubstituted linear alkyl; one or more examples of a fragrance raw material which comprises this unit includes nonanal and decanal;

ii) $C_6$–$C_{22}$, preferably $C_6$–$C_{18}$, more preferably $C_6$–$C_{15}$ substituted or unsubstituted branched alkyl; one or more examples of a fragrance raw material which comprises this unit includes 2-methyldecanal;

iii) $C_6$–$C_{22}$, preferably $C_6$–$C_{18}$, more preferably $C_6$–$C_{15}$ substituted or unsubstituted linear alkenyl; one or more examples of a fragrance raw material which comprises this unit includes 10-undecenal;

iv) $C_6$–$C_{22}$, preferably $C_6$–$C_{15}$, more preferably $C_6$–$C_{18}$ substituted or unsubstituted branched alkenyl; one or more examples of a fragrance raw material which comprises this unit includes citral, melonal, and neral;

v) $C_6$–$C_{22}$, preferably $C_6$–$C_{18}$, more preferably $C_6$–$C_{10}$ substituted or unsubstituted cycloalkyl;

vi) $C_6$–$C_{22}$, preferably $C_6$–$C_{15}$, more preferably $C_6$–$C_{15}$ substituted or unsubstituted branched cycloalkyl;

vii) $C_6$–$C_{22}$, preferably $C_6$–$C_{18}$, more preferably $C_6$–$C_{15}$ substituted or unsubstituted cycloalkenyl;

viii) $C_6$–$C_{22}$, preferably $C_6$–$C_{18}$, more preferably $C_6$–$C_{15}$ substituted or unsubstituted branched cycloalkenyl; one or more examples of a fragrance raw material which comprises this unit includes α-damascone and β-ionone;

ix) $C_6$–$C_{22}$, preferably $C_6$–$C_{18}$, more preferably $C_6$–$C_{10}$ substituted or unsubstituted aryl wherein said aryl unit preferably comprises a phenyl unit; one or more examples of a fragrance raw material which comprises this unit includes benzaldehyde, hydrotropaldehyde and vanillin;

x) $C_6$–$C_{22}$, preferably $C_6$–$C_{15}$, more preferably $C_6$–$C_{15}$ substituted or unsubstituted heterocyclicalkyl;

xi) $C_6$–$C_{22}$, preferably $C_6$–$C_{18}$, more preferably $C_6$–$C_{15}$ substituted or unsubstituted heterocyclicalkenyl;

xii) and mixtures thereof;

$R^b$ is:

i) hydrogen;

ii) $C_1$–$C_{10}$, preferably $C_1$–$C_5$ substituted or unsubstituted linear alkyl;

iii) $C_3$–$C_{10}$, preferably $C_3$–$C_5$ substituted or unsubstituted branched alkyl;

iv) $C_2$–$C_{10}$, preferably $C_2$–$C_5$ substituted or unsubstituted linear alkenyl;

v) $C_3$–$C_{10}$, preferably $C_4$–$G_{10}$ substituted or unsubstituted branched alkenyl;

vi) $C_3$–$C_{15}$, preferably $C_6$–$C_{10}$ substituted or unsubstituted cycloalklyl;

vii) $C_4$–$C_{15}$, preferably $C_6$–$C_{10}$ substituted or unsubstituted branched cycloalkyl;

viii) $C_4$–$C_{15}$, preferably $C_6$–$C_{10}$ substituted or unsubstituted cycloalkenyl;

ix) $C_5$–$C_{15}$, preferably $C_6$–$C_{10}$ substituted or unsubstituted branched cycloalkenyl;
x) $C_6$–$C_{15}$, preferably $C_6$–$C_{10}$ substituted or unsubstituted aryl;
xi) $C_6$–$C_{22}$, preferably $C_6$–$C_{10}$ substituted or unsubstituted heterocyclicalkyl;
xii) $C_6$–$C_{22}$, preferably $C_6$–$C_{10}$ substituted or unsubstituted heterocyclicalkenyl;

$R^a$ and $R^b$ when taken together form a substituted or unsubstituted ring having in the ring from 3 to 10 carbon atoms; one or more examples of which are substituted cyclopentanone derivatives inter alia hedione and nectaryl; and each $R^c$, $R^d$, $R^6$ and each $R^4$ and $R^5$ pair are independently:

i) $R^b$;
ii) hydroxyl;
iii) a carbonyl comprising unit having the formula:

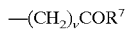

wherein $R^7$ is:
a) —OH, in the case of carboxylic acids;
b) —$OR^8$, in the case of esters wherein $R^8$ is hydrogen; $C_1$–$C_{15}$, preferably $C_1$–$C_{10}$, more preferably $C_1$–$C_4$ substituted or unsubstituted linear alkyl; $C_3$–$C_{15}$, preferably $C_3$–$C_{10}$, more preferably $C_3$–$C_4$ substituted or unsubstituted branched alkyl; $C_2$–$C_{22}$, preferably $C_2$–$C_{10}$, more preferably $C_2$–$C_4$ substituted or unsubstituted linear alkenyl; $C_3$–$C_{22}$ substituted or unsubstituted branched alkenyl, or mixtures thereof;
c) —$N(R^9)_2$ in the case of amides wherein each $R^9$ is independently hydrogen; $C_1$–$C_{15}$, preferably $C_1$–$C_{10}$, more preferably $C_1$–$C_4$ substituted or unsubstituted linear alkyl; $C_3$–$C_{15}$, preferably $C_3$–$C_{10}$, more preferably $C_3$–$C_4$ substituted or unsubstituted branched alkyl; or mixtures thereof;
d) $C_1$–$C_{22}$, preferably $C_1$–$C_5$ substituted or unsubstituted linear alkyl;
e) $C_1$–$C_{22}$, preferably $C_3$–$C_5$ substituted or unsubstituted branched alkyl;
f) $C_2$–$C_{22}$, preferably $C_2$–$C_5$ substituted or unsubstituted linear alkenyl;
g) $C_3$–$C_{22}$, preferably $C_4$–$C_{10}$ substituted or unsubstituted branched alkenyl;
h) $C_5$–$C_{22}$, preferably $C_6$–$C_{10}$ substituted or unsubstituted cycloalkyl;
i) $C_6$–$C_{22}$, preferably $C_6$–$C_{10}$ substituted or unsubstituted aryl;
j) $C_6$–$C_{22}$, preferably $C_6$–$C_{10}$ substituted or unsubstituted heterocyclicalkyl;
k) $C_6$–$C_{22}$, preferably $C_6$–$C_{10}$ substituted or unsubstituted heterocyclicalkenyl;
the index v is from 0 to 22;
v) alkyleneoxy units having the formula:

wherein each $R^{10}$, $R^{11}$, and $R^{12}$ is independently;
a) hydrogen;
b) —OH;
c) $C_1$–$C_4$ alkyl, preferably methyl;
d) or mixtures thereof; preferably $R^{10}$, $R^{11}$, and $R^{12}$ are each hydrogen;
$R^{13}$ is:
a) hydrogen;
b) $C_1$–$C_4$ alkyl, preferably methyl;
c) or mixtures thereof; preferably $R^{13}$ is methyl or hydrogen, more preferably hydrogen;
$R^{14}$ is:
a) hydrogen;
b) $C_1$–$C_4$ alkyl, preferably methyl;
c) or mixtures thereof; preferred $R^{14}$ is hydrogen;
$R^{10}$ and $R^{11}$ when taken together form a $C_3$–$C_6$ spiroannulated ring, carbonyl unit, or mixtures thereof; y has the value from 0 to 10, z has the value from 1 to 50;
vi) any two $R^c$, $R^d$, $R^4$, $R^5$, or $R^6$ units when taken together, and where feasible, combined to form:
a) a carbonyl moiety;
b) a $C_3$–$C_6$ spiroannulated ring;
c) a heterocyclic aromatic ring comprising from 5 to 7 atoms;
d) a non-heterocyclic aromatic ring comprising from 5 to 7 atoms;
e) a heterocyclic ring comprising from 5 to 7 atoms;
f) a non-heterocyclic ring comprising from 5 to 7 atoms;
g) or mixtures thereof;
vii) and mixtures thereof;
the index n is an integer from 1 to 3, preferably 1 or 2, more preferably 1.

For the purposes of the present invention, the term "substituted" is defined herein as "compatible moieties which replace a hydrogen atom". For the purposes of the present invention, hydrogens which are substitutable are labeled as R' units in the following examples. Non-limiting examples of substituents which can replace hydrogen atoms are $C_1$–$C_{22}$ linear or branched hydrocarbyl units inter alia alkyl, alkenyl; hydroxy, nitrilo, nitro, carboxyl (—CHO; —$CO_2H$; —$CO_2R''$; —$CONH_2$; —$CONHR''$; —$CONR''_2$; wherein R" is $C_1$–$C_{12}$ linear or branched alkyl), amino, $C_1$–$C_{12}$ mono- and dialkylamino, and mixtures thereof. However, the formulator may wish to include other substituents not specifically mentioned herein. Not each hydrogen of a substituted unit, i.e., substituted linear alkyl, must be substituted; only one hydrogen must be substituted by another moiety for a unit to be "substituted" for the purposes of the present invention.

FRAGRANCE DELIVERY SYSTEMS

The present invention also relates to fragrance raw material delivery systems, said delivery systems comprising:

A) from about 0.1%, preferably from about 0.5%, more preferably from about 1%, yet more preferably from about 5%, most preferably from about 10% to about 100%, preferably to about 75%, more preferably to about 50% by weight, of a pro-fragrance component comprising:

i) at least 0.01%, preferably from about 0.5%, more preferably from about 5%, most preferably from about 25% to about 100%, more preferably to about 75%., most preferably to about 50% by weight, of an β-amino ketone pro-fragrance component according to the present invention;

ii) optionally from about 0.01%, preferably from about 0.5%, more preferably from about 5%, most preferably from about 25% to about 99%, more preferably to about 75%, most preferably to about 50% by weight, by weight, of one or more pro-accords formed from at least one fragrance raw material, wherein said pro-accord is selected from the group consisting of acetals, ketals, orthoesters, orthocarbonates, and mixtures thereof, each proaccord releasing upon hydrolysis said fragrance raw material from which it is formed, said fragrance raw materials selected from the group consisting of primary, secondary, and tertiary alcohols, aldehydes, ketones, esters, carbonates, and mixtures thereof, provided at least one pro-accord:
   a) is formed from at least one fragrance raw material having a molecular weight greater than or equal to about 100 g/mol;
   b) has a fragrance release half-life of greater than or equal to about 0.1 hours at pH 5.3 and less than or equal to about 12 hours at pH 2.5 when measured in $NaH_2PO_4$ buffer;
   iii) the balance carriers, stabilizers, and other adjunct ingredients; and
B) optionally from about 0.01%, preferably from about 0.5%, more preferably from about 1%, yet more preferably from about 5%, most preferably from about 10% to about 99%, preferably to about 75%, more preferably to about 50% by weight, by weight, a fragrance raw material component comprising:
   i) optionally at least 0.01%, preferably from about 0.5%, more preferably from about 5%, most preferably from about 25% to about 100%, more preferably to about 75%, most preferably to about 50% by weight, by weight, of a mixture of one or more base note fragrances:
   ii) optionally at least 0.01%, preferably from about 0.5%, more preferably from about 5%, most preferably from about 25% to about 100%, more preferably to about 75%, most preferably to about 50% by weight, by weight, of a mixture of one or more top or middle note fragrances;
   iii) optionally the balance carriers, fixatives, and other adjunct ingredients.

When used the fragrance delivery systems of the present invention will comprise from about 0.1%, preferably from about 1% to about 100%, preferably to about 85% of the composition depending upon the execution. For example, a fine fragrance may comprise 100% by weight, of a fragrance delivery as described herein, whereas a body lotion or cream may comprise from about 1% to about 5% by weight, of the fragrance delivery system.

For the purposes of the fragrance delivery systems of the present invention, a "pro-accord which comprises n fragrance raw materials but which releases n+1 fragrance raw materials" is defined as "a compound which is prepared from one or more fragrance raw materials, said fragrance raw material being chemically transformed into a "releasable form" such that when said releasable form breaks down, the original fragrance raw material is released as well as at least one other fragrance raw material which was not a starting material used in forming the releasable form". The term "releasable form" is defined herein as a "pro-fragrance or pro-accord compound, which ever form is applicable". Non-limiting examples of "releasable forms" or pro-accords which satisfy the n+1 requirement are as follows.

Preferably the pro-accords of the present invention are orthoesters and orthocarbonates which deliver n+1 fragrance raw materials when the "pro-accord" has been formed from n fragrance raw materials. These "Increased Release" pro-accords are preferably formate, acetate, propionate, and benzoate orthoesters. Any fragrance raw material may be used to form the "increased release" pro-accord provided the final pro-accord:
   a) has a molecular weight greater than or equal to about 300 g/mol;
   b) has a molecular weight at least two times greater than the lowest molecular weight fragrance raw material which comprises said pro-accord; and
   c) has a fragrance release half-life greater than or equal to about 0.1 hours when measured in $NaH_2PO_4$ buffer at pH 5.3 and less than about 12 hours when measured in $NaH_2PO_4$ buffer at pH 2.5.

The value of the index n is an integer from 1 to 3.

When present the "increased release" pro-accords comprise at least 0.01% of the increased fragrance retention composition, preferably at least about 0.1% more preferably at least about 0.5% by weight, of said composition. More than one "increased release" pro-accords may be combined together as described herein above to provide a complex perfume mixture or accord.

Non-limiting examples of pro-accords which optionally comprise the fragrance delivery systems of the present invention include orthoesters having the formula:

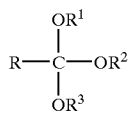

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$, $R^2$ and $R^3$ are independently $C_1$–$C_{20}$ linear, branched, or substituted alkyl; $C_2$–$C_{20}$ linear,branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof; or a cyclic orthoester having the formula:

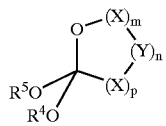

wherein at least one $R^4$ or $R^5$ is derived from a fragrance raw material alcohol, each X is —$C(R^6)_2$— wherein each $R^6$ is independently hydrogen, $C_1$–$C_{22}$ linear or branched alkyl, $C_2$–$C_{22}$ linear or branched alkenyl, $C_6$–$C_{22}$ substituted or unsubstituted aryl, and mixtures thereof, Y is —$CR^7R^8$—, C=O, and mixtures thereof, wherein $R^7$ and $R^8$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^7$ and $R^8$ can be taken together to form a spiroannulated ring or taken together with any $R^6$ to form a fused ring, said spiroannulated or fused ring having from 3 to 8 carbons and optionally one or more heteroatoms in said ring, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; m is from 0 to 14, p is from 0 to 14, and n is from 0 to 3; provided m+n+p is at least 1 and less than or equal to 14.

Examples of "increased release" pro-accords which are comprised of a single fragrance raw materials but which release at least 2 fragrance raw materials include but are not limited to tris(citronellyl)orthoformate which releases the binary accord citronellyl formate/citronellol; tris(citronellyl) orthoacetate which releases the binary accord citronellol/ citronellyl acetate; tris(geranyl)orthoformate which releases the binary accord geraniol/geranyl formate; tris(geranyl) orthoacetate which releases the binary accord geraniol/ geranyl acetate; tris(phenylethyl)orthoformate which releases the binary accord 2-phenylethanol/phenylethyl formate; tris(phenylethyl)orthoacetate which releases the binary accord 2-phenylethanol/phenylethyl acetate; tris(9-decenyl)orthoformate which releases the binary accord 9-decen-1-ol/9-decenyl formate; and tris(9-decenyl) orthoacetate which releases the binary accord 9-decen-1-ol/ 9-decenyl acetate. For the purposes of the present invention when an orthoester comprises only one fragrance raw material alcohol (releases a binary accord) the terms "tris (alcohol)orthoester" and "alcohol orthoester" are used interchangeably. For example, tris(geranyl)orthoacetate stands equally well for geranyl orthoacetate and are considered interchangeable.

The pro-accord tris(9-decenyl)orthoformate is prepared by treating 9-decenol (i.e., Rosalva), which is a fragrance raw material as defined herein, with a suitable amount of triethyl orthoformate, not a fragrance raw material as defined herein, in the presence of an acid catalyst optionally in the presence of a solvent. Tris(9-decenyl) when exposed to suitable conditions (e.g., exposure to the acid mantle of human skin) breaks down to release a mixture of 9-decenol and 9-decenyl formate, both of which are fragrance raw materials. Therefore, one fragrance raw material is used to prepare a releasable form (pro-accord) of two fragrance raw materials.

The pro-accord 3,7-dimethyl-1,6-octadien-3-yl 3-(naphthyl)-3-oxo-propionate, which is a β-ketoester proaccord, is prepared by treating 3,7-dimethyl-1,6-octadien-3-ol (linalool), which is a fragrance raw material according to the present invention, with diketene under suitable conditions to form intermediate 3,7-dimethyl-1,6-octadien-3-yl 3-oxo-butyrate, which is subsequently treated with 2-naphthoyl chloride to yield the pro-accord. 3,7-Dimethyl-1,6-octadien-3-yl 3-(β-naphthyl)-3-oxo-propionate when exposed to suitable conditions (e.g., exposure to nascent moisture) breaks down to release a mixture of linalool and methyl β-naphthyl ketone, both of which are fragrance raw materials as defined herein.

As described herein above, an optional component of the fragrance delivery systems of the present invention are pro-fragrances or pro-accords which are not heterocyclic aldehyde and/or ketone releasing pro-fragrances. The optional pro-accords or pro-fragrances are equally functional in either personal care compositions inter alia lotions, creams, deodorants or personal fragrance compositions inter alia fine fragrances, perfumes.

Preferred optional pro-accords and/or pro-fragrances include, but are not limited to, orthoesters, orthocarbonates, acetals, ketals, ortholactones, and β-ketoesters.

Non-limiting examples of optional orthoesters which are suitable for use in the fragrance delivery systems of the present invention include tris-geranyl orthoformate, tris(cis-3-hexen-1-yl)orthoformate, tris(phenylethyl)orthoformate, bis(citronellyl)ethyl orthoacetate, tris(citronellyl) orthoformate, tris(cis-6-nonenyl)orthoformate, tris (phenoxyethyl)orthoformate, tris(geranyl,neryl) orthoformate (70:30 geranyl:neryl), tris(9-decenyl) orthoformate, tris(3-methyl-5-phenylpentanyl) orthoformate, tris(6-methylheptan-2-yl)orthoformate, tris ([4-(2,2,6-trimethyl-2-cyclohexen-1-yl)-3-buten-2-yl] orthoformate, tris[3-methyl-5-(2,2,3-trimethyl-3-cyclopenten-1-yl)-4-penten-2-yl]orthoformate, trismenthyl orthoformate, tris(4-isopropylcyclohexylethyl-2-yl) orthoformate, tris-(6,8-dimethylnonan-2-yl)orthoformate, tris-phenylethyl orthoacetate, tris(cis-3-hexen-1-yl) orthoacetate, tris(cis-6-nonenyl)orthoacetate, tris-citronellyl orthoacetate, bis(geranyl)benzyl orthoacetate, tris(geranyl) orthoacetate, tris(4-isopropylcyclohexylmethyl) orthoacetate, tris(benzyl)orthoacetate, tris(2,6-dimethyl-5-heptenyl)orthoacetate, bis(cis-3-hexen-1-yl)amyl orthoacetate, and neryl citronellyl ethyl orthobutyrate.

Non-limiting examples of optional orthocarbonates which are suitable for use in the fragrance delivery systems of the present invention include bis(ethyl) bis(geranyl) orthocarbonate, bis(ethyl) bis(phenylethyl)orthocarbonate, bis(ethyl) bis(cis-3-hexenyl)orthocarbonate, bis(ethyl) bis (citronellyl)orthocarbonate, bis(ethyl) bis(linalyl) orthocarbonate, bis(ethyl) bis(menthyl)orthocarbonate, bis (dodecyl) bis(geranyl)orthocarbonate, and bis(dodecyl) bis (phenylethyl)orthocarbonate.

Non-limiting examples of optional acetals which are suitable for use in the fragrance delivery systems of the present invention include bis(cis-3-hexenyl)vanillin, bis (geranyl)cinnamaldehyde acetal, bis(2-phenylethyl) anisaldehyde acetal, bis(citronellyl)cyclamen aldehyde acetal, and bis(citronellyl)citral acetal.

Non-limiting examples of optional ketals which are suitable for use in the fragrance delivery systems of the present invention include bis(linalyl)β-ionone ketal, bis (dihydromyrcenyl)α-damascone ketal, bis(linalyl)6,7-dihydro-1,1,2,3,3-pentamethyl-4(5H)-indanone ketal, bis (dihydromyrcenyl)β-ionone ketal, and bis(citronellyl)cis-jasmone ketal.

Non-limiting examples of optional β-ketoesters which are suitable for use in the fragrance delivery systems of the present invention include 2,6-dimethyl-7-octen-2-yl 3-(4-methoxyphenyl)-3-oxo-propionate, 3,7-dimethyl-1,6-octadien-3-yl 3-(α-naphthyl)-3-oxo-propionate, 2,6-dimethyl-7-octen-2-yl 3-(4-methoxyphenyl)-3-oxo-propionate, cis 3-hexen-1-yl 3-(β-naphthyl)-3-oxo-propionate 2,6-dimethyl-7-octen-2-yl 3-(nonanyl)-3-oxo-propionate, 2,6-dimethyl-7-octen-2-yl 3-oxo-butyrate 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, and 3,7-dimethyl-2,6-octadienyl 3-heptyl-3-oxo-propionate.

An example of a fragrance delivery system according to the present invention comprises:
a) from about 0.1% by weight, of a β-amino ketone pro-fragrance, for example, 1-(2,6,6-trimethyl-3-cyclohexen-1-yl)-3-N,N-bis(5-hydroxy-3-oxapentyl)-1-butanone;
b) from about 0.2% by weight, of one or more aldehyde releasing pro-fragrances, for example, 2-(6-methyl-5- hepten-2-yl)-3-(1-methylethyl)-4-oxazikudubecarboxylic acid methyl ester, 2-(2,4-dimethyl-3-cyclohexen-1-yl)-3-(1-methylethyl)4-oxazolidinecarboxylic acid methyl ester;

c) optionally from about 0.1% by weight, of one or more alcohol releasing pro-fragrances; preferably an alcohol releasing pro-accord, for example, geranyl orthoformate;

d) from about 0.1% by weight, of one or more fragrance raw materials, for example, lillial, γ-decalactone;

e) optionally, from about 1% by weight, of pre-blended perfume ingredients of fragrance raw material accords; and f) the balance carriers.

A non-limiting example of an alcohol releasing pro-accord admixture which is suitable for use in the fragrance delivery systems of the present invention comprises:

i) from about 0.5% to about 5% by weight, of nonadyl orthoformate;

ii) from about 1.5% to about 5% by weight, of mugetanol orthoformate;

iii) from about 1.5% to about 5% by weight, of osyrol orthoformate; and iv) from about 1% to about 10% by weight, of benzyl orthoacetate.

Fragrance Release Half-life

One aspect of the present invention which is a key element in providing the formulator with a method for determining the manner in which a pro-fragrance according to the present invention releases its fragrance raw material, is the measurement of the pro-fragrance "Fragrance Release Half-Life, (FRHL). The pro-fragrances useful in the personal care compositions of the present invention generally have a delayed release of final fragrance raw material in order to achieve the increased fragrance longevity benefits described herein. However, the pro-fragrances generally also deliver the fragrance raw materials during a time period useful to the formulator, for example, within a time period desirable to the consumer.

For the purposes of the present invention the pro-accords generally have a FRHL of less than or equal to 12 hours when measured in $NaH_2PO_4$ buffer at pH 2.5 and greater than or equal to 0.1 hour when measured in $NaH_2PO_4$ buffer at pH 5.3. The "Fragrance Release Half-life" is defined herein as follows.

Pro-fragrances deliver their corresponding mixture of fragrance raw materials or fragrance accords according to the equation:

Pro-Fragrance→Fragrance Raw Material wherein the fragrance raw material which is released may be released as a single component or a multiple fragrance raw material accord.

The rate at which the fragrance is released is defined by the formula:

Rate=k[Pro-fragrance]

and can be further expressed by the formula:

$$-\frac{d[\text{Pro-fragrance}]}{dt} = k[\text{Pro-fragrance}]$$

wherein k is the release rate constant and [Pro-fragrance] is the concentration of pro-fragrance. For the purposes of the present invention the "Fragrance Release Half-life", $t_{1/2}$, is related to the release rate constant by the formula:

$$t_{1/2} = \frac{0.693}{k}$$

and this relationship is used for the purposes of the present invention to determine the "FRHL.

Due to the hydrophobic nature of some pro-accords, it is necessary to conduct the determination of $t_{1/2}$ and k in a mixture of 90/10 dioxane/phosphate buffered water. The phosphate buffered water is prepared by admixing 3.95 mL of 85% phosphoric acid ($H_3PO_4$) and 24 g of sodium dihydrogen phosphate ($NaH_2PO_4$) with one liter of water. The pH of this solution is approximately 2.5. Next 10 mL of the phosphate buffer is admixed with 90 mL of dioxane and the pro-fragrance to be analyzed is added. The hydrolysis kinetics are then monitored by conventional HPLC at 30° C.

In some instances, it is desirable to formulate a fragrance delivery system having one or more pro-fragrances which deliver a rapid release of fragrance raw material in addition to the delayed onset of a fragrance. In such cases the hydrolysis rate, and therefore the determination of $t_{1/2}$ must be measured in a buffer system which can accommodate this more rapid hydrolysis rate.

The pro-fragrances of the present invention are stable under pH conditions encountered in the formulation and storage of fine perfume, personal care and personal hygiene articles which have a pH of from about 7.1 to 11.5, and during solution-use of such products. Due to their high molecular weight and hydrophobicity, these pro-fragrances and/or pro-accords remain deposited upon skin even when exposed to water (i.e. when formulated into a sun screen). Because the pro-fragrances are subject to hydrolysis when the pH is reduced, they hydrolyze to release their component fragrance compounds when applied to skin or are exposed even to reduced pH such as present in air and humidity. The reduction in pH should be at least 0.1, preferably at least about 0.5 units. Preferably the pH is reduced by at least 0.5 units to a pH of 7.5 or less, more preferably 6.9 or less. Preferably, the solution in which the pro-accord is applied is alkaline.

Odor Value

The pro-fragrances of the present invention typically have an Odor Value greater than or equal to about 1, preferably greater than or equal to about 5, more preferably greater than or equal to about 10. The term "Odor Value" is defined by the following formula:

$$OV = \frac{[\text{Concentration of FRM}]}{ODT}$$

wherein OV is the odor value of the fragrance raw material released upon the skin by the pro-accord. The odor value is the concentration of the fragrance raw material, FRM, on the skin surface divided by the Odor Detection Threshold, ODT. The term "level of noticeability" is often applied to and/or substituted for the term "odor value".

Odor Detection Threshold

For the purposes of the present invention the term "odor detection threshold" is defined as the level at which a fragrance raw material is perceptible to the average human. The odor detection threshold (ODT) of the compositions of the present invention are preferably measured by carefully controlled gas chromatograph (GC) conditions as described hereinbelow. The preferred fragrance raw materials of the present invention have an ODT of at least about 100 part per billion (ppb), more preferably 10 ppb, most preferably 1 ppb. Fragrance raw materials having an ODT greater than 10 parts per million (ppm) are typically avoided unless useful as an adjunct ingredient, for example, as an adjunct alcohol when adjusting the fragrance release half-life of an orthoester.

Determination of Odor Detection Thresholds is as follows. A gas chromatograph is characterized to determine the exact volume of material injected by a syringe, the precise split ratio, and the hydrocarbon response using a hydrocarbon standard of known concentration and chain-length distribution. The air flow rate in accurately measured and, assuming the duration of a human inhalation to last 0.02 minutes, the sampled volume is calculated. Since the precise concentration at the detector at any point in time is known, the mass per volume inhaled is known and hence the concentration of material. To determine whether a material has a threshold below 10 ppb, solutions are delivered to the sniff port at the back-calculated concentration. A panelist sniffs the GC effluent and identifies the retention time when odor is notice. The average over all panelists determines the threshold of noticeability or ODT. The necessary amount of analyte is injected onto the column to achieve a 10 ppb concentration at the detector. Typical gas chromatograph parameters for determining odor detection thresholds are listed below.

GC: 5890 Series II with FID detector 7673 Autosampler
Column: J&W Scientific DB-1, length 30 m, i.d. 0.25 mm, film thickness 1 μm.
Split Injection: 17/1 split ratio
Autosampler: 1.13 μl/injection
Column flow: 1.10 mL/min
Air flow: 345 mL/min
Inlet temperature: 245° C.
Detector temperature: 285° C.
Temperature Information:
- Initial temperature: 50° C.
- Rate: 5° C./min
- Final temperature: 280° C.
- Final time: 6 min Leading assumptions: 0.02 minutes per sniff and that GC air adds to sample dilution.

Skin Performance Index

Although a pro-fragrance or pro-accord may comprise a fragrance release half-life which ensures delivery of a fragrance raw material during a period of time useful to the formulator, unless the fragrance raw materials which comprise said fragrance delivery system have ODT values large enough to be perceived by the user, the formulator will be compelled to use an inordinate amount of material to achieve a suitable fragrance level.

The pro-fragrances of the present invention have a Skin Performance Index (SPI) greater than or equal to 0.1, preferably greater than or equal to 0.5. The Skin Performance Index is defined by the following:

$$SPI = \frac{[Odor\ Value]^*}{t_{1/2}}$$

wherein the term [Odor Value]* is the estimated concentration of the fragrance raw material in the headspace above a solution of the fragrance raw material as measured in a 1% solution of ethanol, and $t_{1/2}$ is the fragrance release half-life measured at pH 5.3 in the above described buffer. For the purposes of the present invention, the $t_{1/2}$ of the SPI is measured at 5.3 and the value of the fragrance release half-life is preferably from 0.1 hours to 60 hours.

The [Odor Value]* is an estimation of the vapor pressure of the fragrance raw material using empirically determined KOVATS indices. "The Vapor Pressures of Pure Substances", T. Boublik et al., Elseiver, N.Y. (1973) incorporated herein by reference, describes an index line for normal alkanes wherein $C_{10}$ is equal to 30,000 ppb, $C_{12}$ is equal to 3,000 ppb, $C_{14}$ is equal to 300 ppb, $C_{16}$ is equal to 30 ppb, etc. Using these values as reference standards, the KOVATS index of a fragrance raw material is obtained from gas chromatographic analysis of the FRM and the experimental index is then used to determine the relative vapor pressure and hence the head space concentration of the fragrance raw material.

"New Method for Estimating Vapor Pressure by the Use of Gas Chromatography" J. Chromatography A, 79 p 123–129, (1996) and "Simple and Versatile Injection System for Capillary Gas Chromatographic Columns: Performance Evaluation of a System Including Mass Spectrometric and Light Pipe Fourier-Transform Infrared Detection", J. Chromatography A, 713, p 201–215, (1996) included herein by reference, further describe methods and techniques suitable for use in determining the vapor pressure and head space concentration of FRM's as they relate to the term [Odor Value]* of the present invention.

Using the criteria set forth in the present invention inter alia fragrance release half-life, odor value, odor detection threshold, skin performance index, the formulator is able to fashion an aldehyde or ketone releasing cyclic pro-fragrance. By manipulation of the $R^2$, $R^3$, $R^4$, $R^5$ and $R^6$ units of the cyclic pro-fragrances of the present invention the release rate of either an aldehyde or ketone fragrance raw material can be adjusted. Several different pro-fragrances which release the same fragrance raw material, but at differing rates or levels, can be admixed to further prolong or extend the period of fragrance raw material delivery.

When present, the carriers, fixatives, or stabilizers will comprise the balance of the compositions. Typical carriers are methanol, ethanol (preferred), iso-propanol, polyethylene glycol, as well as water in some instances, especially as a vehicle to deliver materials which provide reserve alkalinity to the fragrance delivery system. Fixatives serve to lower the volatility of certain top and middle notes in order to extend their contact time on skin. Adjunct ingredients include perfume raw material components which are essential oils and are therefore not a single chemical entity. In addition, the adjunct ingredients may be mixtures of materials which serve a purpose in addition to providing a pleasurable odor (i.e., an astringent in a personal hygiene article).

The formulators, in addition to selected fragrance raw materials, can combine a pre-blended fragrance with the pro-fragrances of the present invention. For the purposes of the present invention the term "pre-blended fragrance" is defined as an existing fragrance accord, commercially available or otherwise, which is enhanced by or in turn enhances the fragrance delivered by the pro-fragrances and/or pro-accords which comprise the balance of the fragrance delivery system. For example, an existing fragrance accord may be suitable in the short term but due to differential evaporation of the most volatile components, high notes, inter alia, the fragrance diminishes or the bouquet shifts. Therefore, pro-fragrances and pro-accords are combined which will release said volatile components thereby sustaining the complete fragrance accord.

The following is a non-limiting example of a β-amino ketone pro-fragrance according to the present invention.

EXAMPLE 1

1-(2,6,6-Trimethyl-3-cyclohexen-1-yl)-3-N-(2-hydroxyethyl)-N-phenylmethyl-1-butanone The damascone releasing β-amino ketone pro-fragrance adduct is prepared by stirring 1 equivalent of δ damascone with 2 equivalents of N-benzylethanolamine until complete as indicated suitable analytical method inter alia, thin layer chromatography, $^1$H NMR. The product is purified by column chromatography on Aluminum Oxide (activated, basic, Brockman I, standard grade, 150 mesh, 58 angstrom) using a mobile phase consisting of 50% hexane, 49% chloroform and 1% triethylamine. Solvents are removed in vacuo and the product is placed under high vacuum (0.10 mm Hg) for 24 hours with stirring to remove any residual solvent to yield the desired β-amino ketone pro-fragrance.

The following are examples of fine fragrance compositions which comprise the fragrance delivery system of the present invention.

TABLE I

| | Weight % | | | |
|---|---|---|---|---|
| Ingredients | 2 | 3 | 4 | 5 |
| β-Amino ketone pro-fragrance[1] | 0.4 | 0.8 | — | — |
| β-Amino ketone pro-fragrance[2] | — | — | 0.3 | 0.6 |
| Pro-fragrance[3] | 0.2 | 0.4 | — | — |
| Pro-fragrance[4] | 0.2 | 0.4 | — | — |
| Pro-fragrance[5] | — | — | 0.6 | 0.2 |
| Pro-fragrance[6] | — | — | — | 0.2 |
| Pre-formulated accords[7] | 14.0 | 14.0 | 14.0 | 14.0 |
| Fragrance raw material[8] | 1.98 | 1.98 | — | — |
| Fragrance raw material[9] | 0.02 | 0.02 | — | — |
| Carrier[10] | balance | balance | balance | balance |

[1]·1-(2,6,6-trimethyl-3-cyclohexen-1-yl)-3-N,N-bis(5-hydroxy-3-oxapentyl)-1-butanone.
[2]·1-(2,6,6-trimethyl-3-cyclohexen-1-yl)-3-N,N-bis(2-hydroxyethyl)-1-butanone.
[3]·2-(2,4-dimethyl-3-cyclohexen-1-yl)-3-(1-methylethyl)4-oxazolidinecarboxylic acid methyl ester.
[4]·2-(6-methyl-5-hepten-2-yl)-3-(1-methylethyl)-4-oxazolidinecarboxylic acid methyl ester.
[5]·Tris(geranyl) orthoformate.
[6]·Benzyl bis(geranyl) orthoformate.
[7]·Admixture of one or more fragrance raw materials having a pro-fragrance enhancing of compatible bouquet.
[8]·Lilial.
[9]·γ-decalactone.
[10]·Ethanol.

What is claimed is:
1. A composition comprising:

A) from 0.01% by weight, of a pro-fragrance component comprising:
   a) at least 0.01% by weight, of an β-amino ketone pro-fragrance component, said pro-fragrance having the formula:

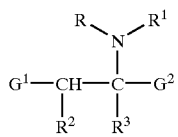

wherein $G^1$ is —CN, —C(O)$Y^1$, —CO$_2Y^1$, and mixtures thereof; $G^2$ is $G^1$, $Y^2$, or mixtures thereof; $Y^1$ and $Y^2$ are each independently $C_1$–$C_{18}$ alkyl, $C_1$–$C_{18}$ alkenyl, $C_1$–$C_{15}$ cycloalkyl, $C_1$–$C_{15}$ cycloalkenyl, $C_6$–$C_{15}$ aryl, $C_6$–$C_{15}$ alkyl substituted aryl, and mixtures thereof; R and $R^1$ are each independently $C_1$–$C_{22}$ substituted or unsubstituted, branched or unbranched alkyl, $C_2$–$C_{22}$ substituted or unsubstituted, branched or unbranched alkenyl, $C_2$–$C_{20}$ substituted or unsubstituted, branched or unbranched hydroxyalkyl, $C_7$–$C_{20}$ substituted or unsubstituted alkylenearyl, $C_3$–$C_{20}$ substituted or unsubstituted cycloalkyl, alkyleneoxy units having the formula:

—$(R^4O)_xR^5$ wherein $R^4$ is $C_2$–$C_4$ alkylene, $R^5$ is hydrogen, $C_1$–$C_4$ alkyl, and mixtures thereof, x is from 1 to 6; $C_6$–$C_{20}$ aryl, $C_5$–$C_{20}$ heteroaryl comprising one or more heteroatoms selected from the group consisting of nitrogen, oxygen, sulfur, and mixtures thereof; two of the units $Y^1$, $Y^2$, R or $R^1$ when taken together form one or more aromatic or non-aromatic, heterocyclic or non-heterocyclic, single rings, fused rings, bicyclo rings, spiroannulated rings, or mixtures thereof, said rings comprising from 3 to 20 carbon atoms and one or more heteroatoms selected from the group consisting of nitrogen, oxygen, sulfur, and mixtures thereof; and $R^2$ and $R^3$ are hydrogen;

b) at least 0.01% by weight, of an aldehyde or ketone releasing pro-fragrance component, said pro-fragrance having the formula:

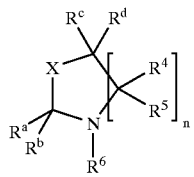

wherein said pro-fragrance or pro-accord releases an aldehyde or a ketone fragrance raw material, wherein X is oxygen or sulfur; $R^a$ is:
  i) $C_6$–$C_{22}$ substituted or unsubstituted linear alkyl;
  ii) $C_6$–$C_{22}$ substituted or unsubstituted branched alkyl;
  iii) $C_6$–$C_{22}$ substituted or unsubstituted linear alkenyl;
  iv) $C_6$–$C_{22}$ substituted or unsubstituted branched alkenyl;
  v) $C_6$–$C_{22}$ substituted or unsubstituted cycloalkyl;
  vi) $C_6$–$C_{22}$ substituted or unsubstituted branched cycloalkyl;
  vii) $C_6$–$C_{22}$ substituted or unsubstituted cycloalkenyl;
  viii) $C_6$–$C_{22}$ substituted or unsubstituted branched cycloalkenyl;
  ix) $C_6$–$C_{22}$ substituted or unsubstituted aryl;

x) $C_6$–$C_{22}$ substituted or unsubstituted heterocyclicalkyl;
xi) $C_6$–$C_{22}$ substituted or unsubstituted heterocyclicalkenyl;
xii) and mixtures thereof;
$R^b$ is:
i) hydrogen;
ii) $C_1$–$C_{10}$ substituted or unsubstituted linear alkyl;
iii) $C_3$–$C_{10}$ substituted or unsubstituted branched alkyl;
iv) $C_2$–$C_{10}$ substituted or unsubstituted linear alkenyl;
v) $C_3$–$C_{10}$ substituted or unsubstituted branched alkenyl;
vi) $C_3$–$C_{15}$ substituted or unsubstituted cycloalkyl;
vii) $C_4$–$C_{15}$ substituted or unsubstituted branched cycloalkyl;
viii) $C_4$–$C_{15}$ substituted or unsubstituted cycloalkenyl;
ix) $C_5$–$C_{15}$ substituted or unsubstituted branched cycloalkenyl;
x) $C_6$–$C_{15}$ substituted or unsubstituted aryl;
xi) $C_6$–$C_{22}$ substituted or unsubstituted heterocyclicalkyl;
xii) $C_6$–$C_{22}$ substituted or unsubstituted heterocyclicalkenyl;
$R^a$ and $R^b$ when taken together form a substituted or unsubstituted ring having in the ring from 3 to 10 carbon atoms; and
each $R^c$, $R^d$, $R^6$ and each $R^4$ and $R^5$ pair are independently:
i) $R^b$;
ii) hydroxyl;
iii) a carbonyl comprising unit having the formula:

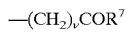

wherein $R^7$ is:
a) —OH;
b) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof;
c) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
d) $C_1$–$C_{22}$ substituted or unsubstituted linear alkyl;
e) $C_1$–$C_{22}$ substituted or unsubstituted branched alkyl;
f) $C_2$–$C_{22}$ substituted or unsubstituted linear alkenyl;
g) $C_3$–$C_{22}$ substituted or unsubstituted branched alkenyl;
h) $C_3$–$C_{22}$ substituted or unsubstituted cycloalkyl;
i) $C_5$–$C_{22}$ substituted or unsubstituted aryl;
j) $C_6$–$C_{22}$ substituted or unsubstituted heterocyclicalkyl;
k) $C_5$–$C_{22}$ substituted or unsubstituted heterocyclicalkenyl;
the index v is from 0 to 22;
iv) alkyleneoxy units having the formula:

wherein each $R^{10}$, $R^{11}$, and $R^{12}$ is independently;
a) hydrogen;
b) —OH;
c) $C_1$–$C_4$ alkyl;
d) or mixtures thereof;

$R^{13}$ is:
a) hydrogen;
b) $C_1$–$C_4$ alkyl;
c) or mixtures thereof;
$R^{14}$ is:
a) hydrogen;
b) $C_1$–$C_4$ alkyl;
c) or mixtures thereof;
$R^{10}$ and $R^{11}$ when taken together form a $C_3$–$C_6$ spiroannulated ring, carbonyl unit, or mixtures thereof; y has the value from 0 to 10, z has the value from 1 to 50;
v) any two $R^c$, $R^d$, $R^4$, $R^5$, or $R^6$ units when taken together form:
a) a carbonyl moiety;
b) a $C_3$–$C_6$ spiroannulated ring;
c) a heterocyclic aromatic ring comprising from 5 to 7 atoms;
d) a non-heterocyclic aromatic ring comprising from 5 to 7 atoms;
e) a heterocyclic ring comprising from 5 to 7 atoms;
f) a non-heterocyclic ring comprising from 5 to 7 atoms;
g) or mixtures thereof;
vi) and mixtures thereof; and
the index n is an integer from 1 to 3; and
B) optionally from 1% by weight, a fragrance raw material component comprising:
i) optionally at least 1% by weight, of a mixture of one or more base note fragrances;
ii) optionally at least 1% by weight, of a mixture of one or more top or middle note fragrances;
iii) optionally the balance carriers, fixatives, and other adjunct ingredients.

2. A composition according to claim 1 wherein R is $C_1$–$C_8$ alkyl, benzyl, and mixtures thereof; $R^1$ is $C_1$–$C_8$ alkyl, $C_1$–$C_4$ hydroxyalkyl, alkyleneoxy units having the formula:

wherein $R^4$ is $C_2$–$C_4$ alkylene, $R^5$ is hydrogen, $C_1$–$C_4$ alkyl, and mixtures thereof, x is from 1–6; and mixtures thereof.

3. A composition according to claim 2 wherein said aldehyde or ketone releasing pro-fragrance component releases a fragrance raw material selected from the group consisting of 4-(4-hydroxy-4-methylpentyl)-3-cyclohexene-1-carboxaldehyde, phenylacetaldehyde, methylnonyl acetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methyl-propanal, 3-(3,4-methylenedioxyphenyl)-2-methylpropan-1-al, 3-(4-ethylphenyl)-2,2-dimethylpropanal, 3-(3-isopropylphenyl) butan-1-al, 2,6-dimethylhep-5-en-1-al, n-decanal, n-undecanal, n-dodecanal, 3,7-dimethyl-2,6-octadien-1-al, 4-methoxybenzaldehyde, 3-methoxy-4-hydroxybenzaldehyde, 3-ethoxy-4-hydroxybenzaldehyde, 3,4-methylenedioxy-benzaldehyde, 3,4-dimethoxybenzaldehyde, and mixtures thereof.

4. A composition according to claim 3 further comprising at least 0.01% by weight, of a pro-accord which releases n+1 fragrances raw materials wherein n is the number of fragrance raw materials from which said pro-accord is formed, n is from 1 to 3.

5. A composition comprising:
a) from 0.1% by weight, of a β-amino ketone pro-fragrance selected from the group consisting of 1-(2, 6,6-trimethyl-3-cyclohexen-1-yl)-3-N,N-bis(5-hydroxy-3-oxapentyl)-1-butanone, 1-(2,6,6-trimethyl-3-cyclohexen-1-yl)-3-N,N-bis(2-hydroxyethyl)-1-butanone, and mixtures thereof;

b) from 0.2% by weight, of an aldehyde releasing pro-fragrances selected from the group consisting of 2-(6-methyl-5-hepten-2-yl)-3-(1-methylethyl)-4-oxazolidinecarboxylic acid methyl ester, 2-(2,4-dimethyl-3-cyclohexen-1-yl)-3-(1-methylethyl)-4-oxazolidinecarboxylic acid methyl ester, and mixtures thereof;

c) optionally from 0.1% by weigh, of one or more alcohol releasing pro-fragrances or pro-accords;

d) from 0.1% by weight, of one or more fragrance raw materials;

e) optionally, from 1% by weigh, of pre-blended perfume ingredients of fragrance raw material accords; and f) the balance carriers.

6. A composition according to claim 5 wherein said alcohol releasing pro-fragrances or pro-accords are selected from the group consisting of tris-geranyl orthoformate, tris(cis-3-hexen-1-yl)orthoformate, tris(phenylethyl) orthoformate, bis(citronellyl)ethyl orthoacetate, tris (citronellyl)orthoformate, tris(cis-6-nonenyl)orthoformate, tris(phenoxyethyl)orthoformate, tris(geranyl,neryl) orthoformate (70:30 geranyl:neryl), tris(9-decenyl) orthoformate, tris(3-methyl-5-phenylpentanyl) orthoformate, tris(6-methylheptan-2-yl)orthoformate, tris ([4-(2,2,6-trimethyl-2-cyclohexen-1-yl)-3-buten-2-yl] orthoformate, tris[3-methyl-5-(2,2,3-methyl-3-cyclopenten-1-yl)-4-penten-2-yl]orthoformate, trismenthyl orthoformate, tris(4-isopropylcyclohexylethyl-2-yl)orthoformate, tris-(6, 8-dimethylnonan-2-yl)orthoformate, tris-phenylethyl orthoacetate, tris(cis-3-hexen-1-yl)orthoacetate, tris(cis-6-nonenyl)orthoacetate, tris-citronellyl orthoacetate, bis (geranyl)benzyl orthoacetate, tris(geranyl)orthoacetate, tris (4-isopropylcyclohexylmethyl)orthoacetate, tris(benzyl) orthoacetate, tris(2,6-dimethyl-5-heptenyl)orthoacetate, bis (cis-3-hexen-1-yl)amyl orthoacetate, and neryl citronellyl ethyl orthobutyrate, and mixtures thereof.

7. A composition according to claim 6 wherein said alcohol releasing pro-fragrances or pro-accords are selected from the group consisting of bis(ethyl) bis(geranyl) orthocarbonate, bis(ethyl) bis(phenylethyl)orthocarbonate, bis(ethyl) bis(cis-3-hexenyl)orthocarbonate, bis(ethyl) bis (citronellyl)orthocarbonate, bis(ethyl) bis(linalyl) orthocarbonate, bis(ethyl) bis(menthyl)orthocarbonate, bis (dodecyl) bis(geranyl)orthocarbonate, and bis(dodecyl) bis (phenylethyl)orthocarbonate, and mixtures thereof.

8. A fine fragrance or perfume comprising:

a) from 0.1% by weight, of a β-amino ketone pro-fragrance selected from the group consisting of 1-(2, 6,6-trimethyl-3-cyclohexen-1-yl)-3-N,N-bis(5-hydroxy-3-oxapentyl)-1-butanone, 1-(2,6,6-trimethyl-3-cyclohexen-1-yl)-3-N,N-bis(2-hydroxyethyl)-1-butanone, and mixtures thereof;

b) from 0.2% by weight, of an aldehyde-releasing pro-fragrances selected from the group consisting of 2-(6-methyl-5-hepten-2-yl)-3-(1-methylethyl)-4-oxazolidinecarboxylic acid methyl ester, 2-(2,4-dimethyl-3-cyclohexen-1-yl)-3-(1-methylethyl)-4-oxazolidinecarboxylic acid methyl ester, and mixtures thereof;

c) optionally from 0.1% by weight, of one or more orthoester pro-accords; and d) the balance carriers.

9. A fine fragrance or perfume according to claim 8 wherein said pro-accords have the formula:

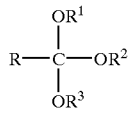

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$, $R_2$ and $R^3$ are independently $C_1$–$C_{20}$ linear, branched or substituted alkyl, $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{24}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof; or a cyclic orthoester having the formula:

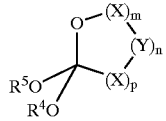

wherein at least one $R^4$ or $R^5$ is derived from a fragrance raw material alcohol, each X is —$C(R^6)_2$— wherein each $R^6$ is independently hydrogen, $C_1$–$C_{22}$ linear or branched alkyl, $C_2$–$C_{22}$ linear or branched alkenyl, $C_6$–$C_{22}$ substituted or unsubstituted aryl, and mixtures thereof, Y is —$CR^7R^8$—, C=O, and mixtures thereof, wherein $R^7$ and $R^8$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^7$ and $R^8$ when taken together form a spiroannulated ring or taken together with any $R^6$ to form a fused ring, said spiroannulated or fused ring having from 3 to 8 carbons and optionally one or more heteroatoms in said ring, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; m is from 0 to 14, p is from 0 to 14, and n is from 0 to 3; provided m+n+p is at least 1 and less than or equal to 14.

10. A fine fragrance or perfume according to claim 9 wherein said orthoester pro-accord is a pro-accord which comprises n fragrance raw materials, said fragrance raw materials having a molecular weight greater than or equal to 100 g/mol and capable of releasing upon hydrolysis n+1 fragrance raw materials, provided said pro-accord:

a) has a molecular weight greater than or equal to 300 g/mol;

b) has a molecular weight at least two times greater than the lowest molecular weight fragrance raw material which comprises said pro-accord; and c) has a fragrance release half-life of greater than or equal to 0.1 hours at pH 5.3 and less than or equal to 12 hours at pH 2.5 when measured in $NaH_2PO_4$ buffer;

wherein n is an integer from 1 to 3.

11. A composition according to claim 1 wherein said β-amino ketone pro-fragrance component has the formula:

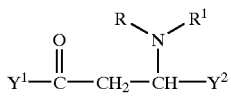

wherein $Y^1$ and $Y^2$ are each methyl or a cycloalkenyl unit selected from the group consisting of:

i) 2,6,6-trimethylcyclohex-2-enyl having the formula:

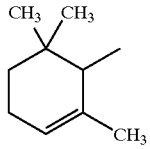

ii) 2,6,6-trimethylcyclohex-1-enyl having the formula:

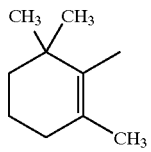

iii) 2-methylene-6,6-dimethylcyclohexanyl having the formula:

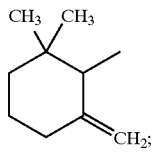

iv) 2,6,6-trimethylcyclohex-3-enyl having the formula:

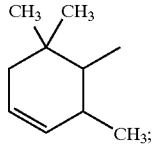

v) and mixtures thereof;
provided at least one $Y^1$ or $Y^2$ is methyl and both $Y^1$ and $Y^2$ are not each methyl, R and $R^1$ are both not hydrogen.

* * * * *

UNITED STATES PATENT AND TRADEMARK OFFICE
CERTIFICATE OF CORRECTION

PATENT NO. : 6,551,987 B1
DATED : April 22, 2003
INVENTOR(S) : Gregory Scott Miracle et al.

It is certified that error appears in the above-identified patent and that said Letters Patent is hereby corrected as shown below:

Column 21,
Lines 53 and 56, "$C_5$-$C_{22}$" should read -- $C_6$-$C_{22}$ --.

Column 24,
Line 17, "$C_2$-$C_{24}$" should read -- $C_2$-$C_{40}$ --.

Signed and Sealed this

Twenty-third Day of December, 2003

JAMES E. ROGAN
*Director of the United States Patent and Trademark Office*